(12) United States Patent
Nakamura et al.

(10) Patent No.: US 10,172,590 B2
(45) Date of Patent: Jan. 8, 2019

(54) ULTRASONIC TRANSDUCER DEVICE AND ULTRASONIC MEASUREMENT DEVICE

(71) Applicant: SEIKO EPSON CORPORATION, Tokyo (JP)

(72) Inventors: Tomoaki Nakamura, Nagano (JP); Jiro Tsuruno, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 716 days.

(21) Appl. No.: 14/831,178

(22) Filed: Aug. 20, 2015

(65) Prior Publication Data

US 2016/0058415 A1    Mar. 3, 2016

(30) Foreign Application Priority Data

Aug. 28, 2014  (JP) .................................. 2014-173769

(51) Int. Cl.
*A61B 8/00*  (2006.01)
*A61B 8/08*  (2006.01)

(52) U.S. Cl.
CPC .......... *A61B 8/4438* (2013.01); *A61B 8/4477* (2013.01); *A61B 8/4483* (2013.01); *A61B 8/5207* (2013.01); *A61B 8/56* (2013.01); *A61B 8/565* (2013.01)

(58) Field of Classification Search
None
See application file for complete search history.

(56) References Cited

U.S. PATENT DOCUMENTS

| | | | | |
|---|---|---|---|---|
| 5,986,382 A | * | 11/1999 | Nysen | G01S 13/755 310/313 D |
| 2003/0111540 A1 | * | 6/2003 | Hartmann | G01V 15/00 235/492 |
| 2004/0220463 A1 | * | 11/2004 | Satoh | A61B 8/00 600/407 |
| 2010/0069730 A1 | * | 3/2010 | Bergstrom | A61B 5/0002 600/365 |
| 2011/0314933 A1 | * | 12/2011 | Mueller | B06B 1/0655 73/861.18 |
| 2013/0308425 A1 | * | 11/2013 | Nakamura | H01L 41/0825 367/87 |

FOREIGN PATENT DOCUMENTS

| | | |
|---|---|---|
| JP | 11-070109 A | 3/1999 |
| JP | 2002-172116 A | 6/2002 |
| JP | 2011-000236 A | 1/2011 |

\* cited by examiner

*Primary Examiner* — Michael Carey
*Assistant Examiner* — Farouk Bruce

(57) ABSTRACT

An ultrasonic transducer device 100 includes a substrate 130, an ultrasonic transducer element array 110 that is provided on the substrate 130 and in which a plurality of ultrasonic transducer elements 111 are arranged, and an identification ultrasonic transducer element array 120 that is provided on the substrate 130 and in which a plurality of identification ultrasonic transducer elements 121 are arranged. Identification information of the ultrasonic transducer device 100 is set by some of the plurality of identification ultrasonic transducer elements 121 being set to a receivable state and the rest being set to a non-receivable state.

16 Claims, 11 Drawing Sheets

ULTRASONIC TRANSDUCER DEVICE AND ULTRASONIC MEASUREMENT DEVICE

BACKGROUND

1. Technical Field

The present invention relates to an ultrasonic transducer device, an ultrasonic measurement device, and the like.

2. Related Art

A biological device such as a health monitor is conceivable that uses an ultrasonic sensor with a thin film piezo-vibrator to measure, for example, the diameter of a blood vessel or the blood flow and thereby obtain a blood pressure and the like. Furthermore, the biological device can also be used as a probe for acquiring information on the inside of the body, that is, for observing the fat thickness, pathological abnormality, and the like.

Biological devices may be used simultaneously by a plurality of users in close proximity, and in the case of measuring the fat thickness for example, the same probe may be used by a plurality of users in a fitness studio or the like. When, in such a situation, cases are considered in which data is managed by a central terminal or is wirelessly transmitted and received for example, each of the devices and probes in use is preferably identifiable using a unique ID.

For example, when stick-on probes are used, a system is likely to be realized in which a plurality of ultrasonic devices operate simultaneously, and it is necessary to determine from which ultrasonic probe a signal is transmitted to the main device.

Meanwhile, JP A-2011-236 discloses an ultrasonic measurement device having a region for storing a unique ID of a probe that is wirelessly connected to the device.

Furthermore, JP A-2002-172116 discloses an ultrasonic probe and an ultrasonic diagnostic device that have, as an ID for example, an 11-bit binary signal based on signal lines being open or grounded, and count the numbers of "0" and "1" as checksums.

Furthermore, JP A-11-70109 discloses an ultrasonic diagnostic device including a pin for detecting probe characteristics.

JP A-2011-236, JP A-2002-172116, and JP A-11-70109 are examples of related art.

As disclosed in JP A-2011-236, JP A-2002-172116, and JP A-11-70109, a method in which a unique ID is given to each probe is known. However, JP A-2011-236 does not specifically mention, to begin with, how to give a probe ID.

Furthermore, a method in which a probe includes an electronically rewritable memory (such as a RAM or EEPROM), and a probe ID is stored in the memory is also conceivable. However, providing such a memory leads to an increase in cost and a risk that the probe ID can easily be rewritten by a third party.

In the methods of JP A-2002-172116 and JP A-11-70109 for example, operation/non-operation of elements is not used when a unique ID is given to each probe, and thus a circuit needs to be adjusted individually, leading to a risk that the circuit may be modified afterwards.

SUMMARY

According to the aspects of the invention, it is possible to provide an ultrasonic transducer device, an ultrasonic measurement device, and the like that includes an identification ultrasonic transducer element, and identification information (a unique ID) is set based on the receivable or non-receivable state of the element, the identification information being less likely to be manipulated and being set by a simple method.

According to an aspect of the invention, an ultrasonic transducer device includes: a substrate; an ultrasonic transducer element array that is provided on the substrate and in which a plurality of ultrasonic transducer elements are arranged; and an identification ultrasonic transducer element array that is provided on the substrate and in which a plurality of identification ultrasonic transducer elements are arranged. Identification information of the ultrasonic transducer device is set by some of the plurality of identification ultrasonic transducer elements being set to a receivable state, and the rest of the plurality of identification ultrasonic transducer elements being set to a non-receivable state.

According to the aspect of the invention, identification information of the ultrasonic transducer device is set by some of the identification ultrasonic transducer elements being set to the receivable state and the rest being set to the non-receivable state. Accordingly, the identification information can be set in a hardware manner by a configuration similar to that of the ultrasonic transducer element for acquiring biological information and the like, making it possible to achieve simple manufacturing and setting of the identification information and the like that is secure against manipulation thereof.

It is preferable that the identification ultrasonic transducer element array include a vibrating membrane formed on the substrate and a piezoelectric element formed on the vibrating membrane. Each of the identification ultrasonic transducer elements that are set to the receivable state is set to the receivable state by a corresponding opening being formed in the substrate, and each of the identification ultrasonic transducer elements that are set to the non-receivable state is set to the non-receivable state by the corresponding opening being not formed in the substrate.

Accordingly, it is possible, for example, to realize setting to the receivable state and the non-receivable state according to whether or not an opening is formed or not formed.

It is preferable that each of the identification ultrasonic transducer elements that are set to the non-receivable state be set to the non-receivable state by a vibration suppression material.

Accordingly, it is possible, for example, to set the element to the non-receivable state using the vibration suppression material.

It is preferable that the plurality of ultrasonic transducer elements be arranged in a first region of the substrate in a plan view in a thickness direction of the substrate, and the plurality of identification ultrasonic transducer elements may be arranged in a second region of the substrate in the plan view.

Accordingly, it is possible to arrange the ultrasonic transducer element array and the identification ultrasonic transducer element array in different regions on the substrate.

It is preferable that the plurality of identification ultrasonic transducer elements be arranged among the plurality of ultrasonic transducer elements.

Accordingly, it is possible to arrange the ultrasonic transducer element array and the identification ultrasonic transducer element array in a mixed manner on the substrate.

It is preferable that the ultrasonic transducer device further include a first signal line for the ultrasonic transducer element array; and a second signal line for the identification ultrasonic transducer element array, the second signal line being different from the first signal line.

Accordingly, it is possible, for example, to use different signal lines for the ultrasonic transducer element array and the identification ultrasonic transducer element array.

According to a further aspect of the invention, an ultrasonic measurement device includes the above-described ultrasonic transducer device.

Accordingly, it is possible, for example, to achieve an ultrasonic measurement device that acquires or uses identification information of the ultrasonic transducer device.

It is preferable that the ultrasonic measurement device further include a processing unit that acquires identification information of the ultrasonic transducer device based on a received signal from the identification ultrasonic transducer element array.

Accordingly, it is possible for the ultrasonic measurement device to acquire identification information of the ultrasonic transducer device.

It is preferable that the processing unit acquire the identification information based on the presence or absent of the received signal from each of the plurality of identification ultrasonic transducer elements.

Accordingly, it is possible to acquire information on whether or not there is a signal from the identification ultrasonic transducer element as the identification information.

It is preferable that the identification ultrasonic transducer element array receive, as the received signal, an echo signal of an ultrasonic wave from the ultrasonic transducer element array, and the processing unit may acquire the identification information based on the received signal received by the identification ultrasonic transducer element array.

Accordingly, it is possible to, for example, acquire identification information based on a received signal received by the identification ultrasonic transducer element array on the basis of an ultrasonic wave transmitted from the ultrasonic transducer element array.

It is preferable that the ultrasonic measurement device further include a communication unit that transmits a received signal received by the ultrasonic transducer element array with the identification information acquired by the processing unit as a header.

Accordingly, it is possible, for example, to transmit the received signal received by the ultrasonic transducer element array and the identification information in an appropriate association with each other to another device.

According to a still further aspect of the invention, an ultrasonic transducer device includes: an ultrasonic transducer element array in which a plurality of ultrasonic transducer elements are arranged. Some of the plurality of ultrasonic transducer elements are set to a receivable state and are connected to a first signal line, and the rest of the plurality of ultrasonic transducer elements are set to a non-receivable state and are connected to a second signal line. Signal terminals connected to the second signal line are electrically independent from the first signal line.

According to the aspect of the invention, different signal lines are used for elements set to the receivable state and for elements set to the non-receivable state, and each signal line is connected to a signal terminal that is electrically independent therefrom. Accordingly, it is possible, for example, to perform processing without mixing outputs from the elements set to the receivable state and outputs from the elements set to the non-receivable state.

DESCRIPTION OF EXEMPLARY EMBODIMENTS

The following describes the present embodiment. Note that the present embodiment described below is not intended to unduly restrict the content of the invention described in the claims. Furthermore, all the configurations explained in the present embodiment are not necessarily essential constituent components of the invention.

1. Method of Present Embodiment

First, a method of the present embodiment will be described. As described above, a method for acquiring various types of biological information using an ultrasonic sensor (ultrasonic transducer element) is known. An ultrasonic transducer device including the ultrasonic transducer element may be, for example, a probe.

In recent years, probes have diversified types, forms, and usages. For example, a probe for use in obtaining a blood pressure and the like by measuring the diameter of a blood vessel or the blood flow takes measurement from the neck or wrist area of a user. The probe for use in such a case may be rod-shaped as conventionally widely used, or band-shaped (for example, wristwatch-shaped) so as to be used by wrapping around a wrist or the like. Alternatively, it is also conceivable that a seal-type probe is attached to a user and used. Furthermore, in the case of a probe for use in observing the fat thickness or a pathological abnormality, various areas (for example, the abdominal area and the chest area) of a user serve as measurement targets, and in this case, various shapes of the probe are also conceivable.

Figure 1:
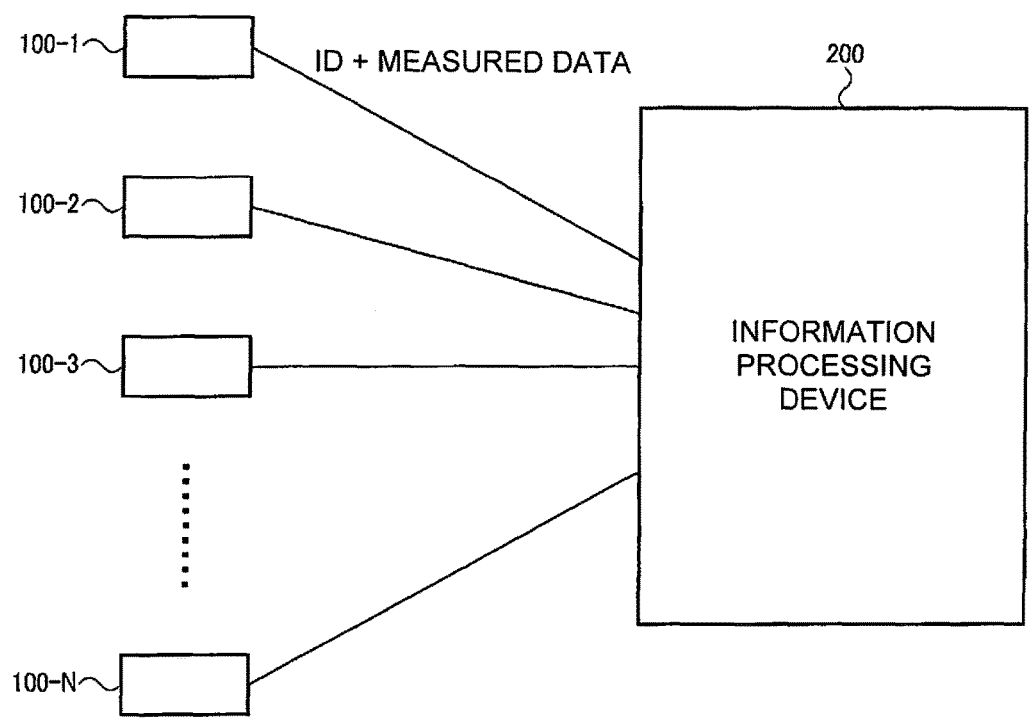
FIG. 1 shows an example of a configuration of a system including ultrasonic transducer devices.

In view of such diversified usage forms, it is necessary to consider a situation, as shown in FIG. 1, that a plurality of probes are simultaneously connected to an information processing device 200 that processes information from the probes. In the example of FIG. 1, first to the N-th ultrasonic transducer devices 100-1 to 100-N are connected to the information processing device 200. The ultrasonic transducer devices and the information processing device 200 may be connected in a wired or wireless manner, but if wireless connection is realizable, this will reduce physical restrictions, and it is thus conceivable that the situation, as shown in FIG. 1, in which multiple probes are simultaneously connected is more likely to occur.

Figure 2A:
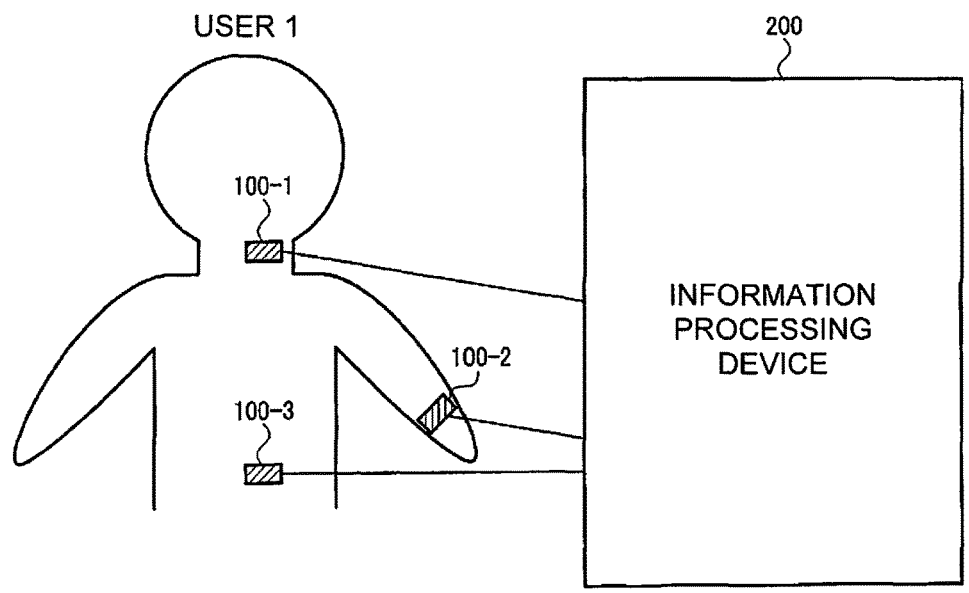
FIGS. 2A and 2B show specific examples of the system including the ultrasonic transducer devices.
Figure 2B:
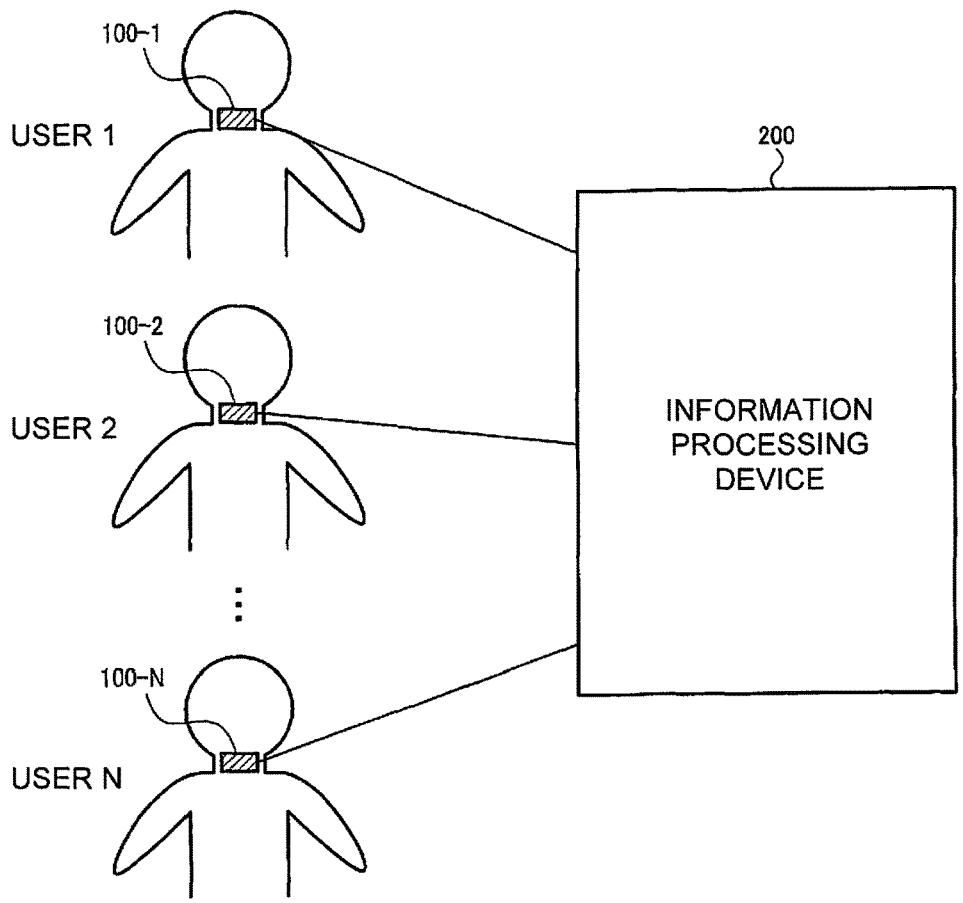

Various specific situations are conceivable, and examples thereof include the situation as shown in FIG. 2A in which a plurality of areas of one user are measured at the same time, and the situation as shown in FIG. 2B in which a plurality of users are measured at the same time. Furthermore, also conceivable is a combination of the cases of FIGS. 2A and 2B in which one or more areas of each of a plurality of users are measured at the same time.

In this case, the information processing device 200 will acquire information from the plurality of ultrasonic transducer devices at the same timing. For example, in the example of FIG. 2A, the information processing device 200 acquires information from an ultrasonic transducer device 100-1 attached to the neck area, an ultrasonic transducer device 100-2 attached to the wrist area, and an ultrasonic transducer device 100-3 attached to the abdominal area.

In FIG. 2A, the information processing device 200 needs to perform processing for obtaining the diameter of a blood vessel (for example, the carotid artery) or the like in the neck area based on the information from the ultrasonic transducer device 100-1, processing for obtaining the diameter of a blood vessel or the like in the wrist area based on the information from the ultrasonic transducer device 100-2, and processing for obtaining a fat or the like in the abdominal area based on the information form the ultrasonic transducer device 100-3 (for example, processing for generating a two-dimensional image). That is, the processing needs to be changed appropriately according to the ultrasonic transducer device from which information is acquired, and thus it is necessary for the information processing device 200 to appropriately determine from which ultrasonic transducer device the acquired information is transmitted. Specifically, if wireless communication with the ultrasonic transducer devices is realized, it will be difficult to identify the device based on information such as a connection port or the like, and thus it is essential to provide an identification method.

Note that in FIG. 2A, the three ultrasonic transducer devices 100-1 to 100-3 respectively measure different areas, and thus it is sufficient, in this example, that the types of the probes can be identified. For example, it is sufficient to perform identification as to whether each probe is for measuring a blood vessel in the neck area, for measuring a blood vessel in the wrist area, or for measuring a fat in the abdominal area, for example. However, a case is also conceivable in which the same user wears a plurality of ultrasonic transducer devices of the same type at the same time, such as a case where two ultrasonic transducer devices for measuring a fat in the abdominal area are attached to different parts of the abdominal area. That is, in a more limited sense, in the case of a plurality of ultrasonic transducer devices of the same type, these devices need to be identified in order to appropriately perform the above-described types of processing.

In the example of FIG. 2B, all N users wear the ultrasonic transducer devices for measuring a blood vessel in the neck area. In this case, making a mistake or the mixing data of the user 1 and data of the user 2 causes a serious problem in administration of biological information. Therefore, also in this case, data acquired from one ultrasonic transducer device needs to be processed in a manner of being clearly separated from the data acquired from another ultrasonic transducer device. Also in this case, it is sufficient that each ultrasonic transducer device is identified. Note that if prevention of a mistake concerning biological information is taken into consideration, personal authentication processing will preferably be performed with respect to each user, but in the present embodiment, identification of the ultrasonic transducer devices without performing personal authentication processing is considered. That is, it is not prohibited to perform personal authentication processing together with the method of the present embodiment, but a description thereof is omitted in the present specification.

As described above, the individual ultrasonic transducer devices need to be identified if appropriate management and processing of the biological information is taken into consideration. In order to do so, a method for assigning a unique ID to each ultrasonic transducer device is conceivable. When information is transmitted from the ultrasonic transducer devices, information (identification information) of the unique ID is also transmitted together, and thereby it is possible to specify an ultrasonic transducer device from which each piece of biological information is transmitted.

However, a method in which an ultrasonic transducer device includes an electronically rewritable memory (such as a RAM or EEPROM), in which a unique ID is stored in the memory, leads to an increase in cost and a risk that the unique ID is easily rewritten by a third party.

Figure 3:
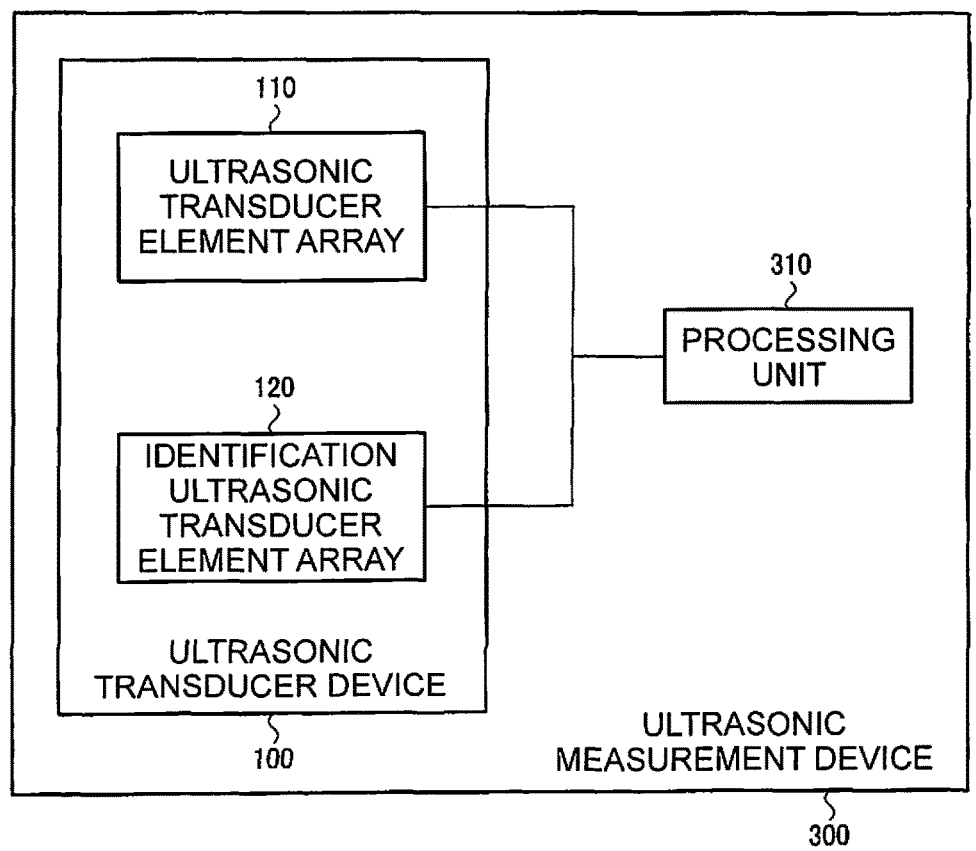
FIG. 3 shows an example of a configuration of the ultrasonic transducer device and an ultrasonic measurement device.
Figure 4:
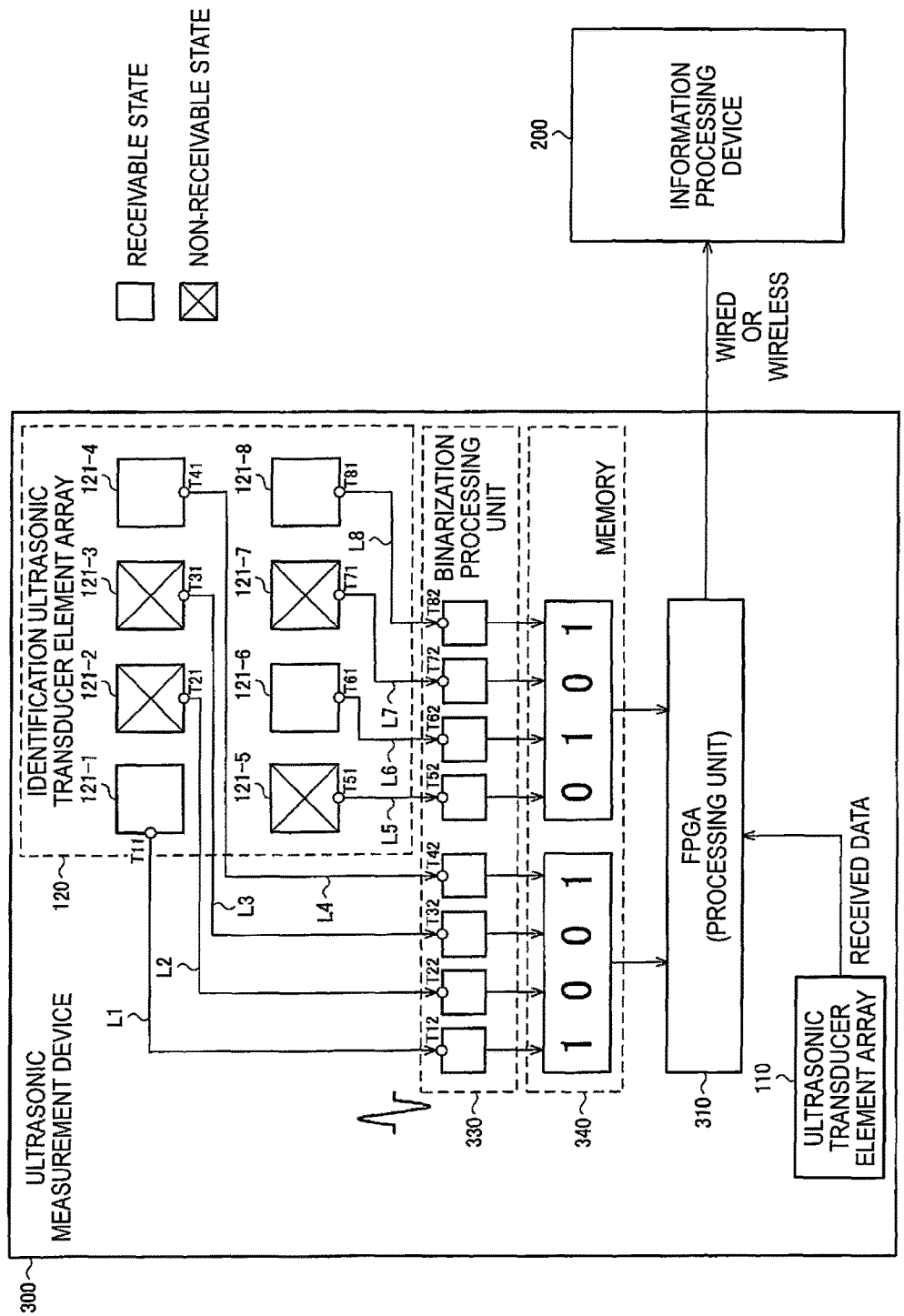
FIG. 4 shows a configuration of the ultrasonic measurement device, and a method for setting identification information.
Figure 9A:
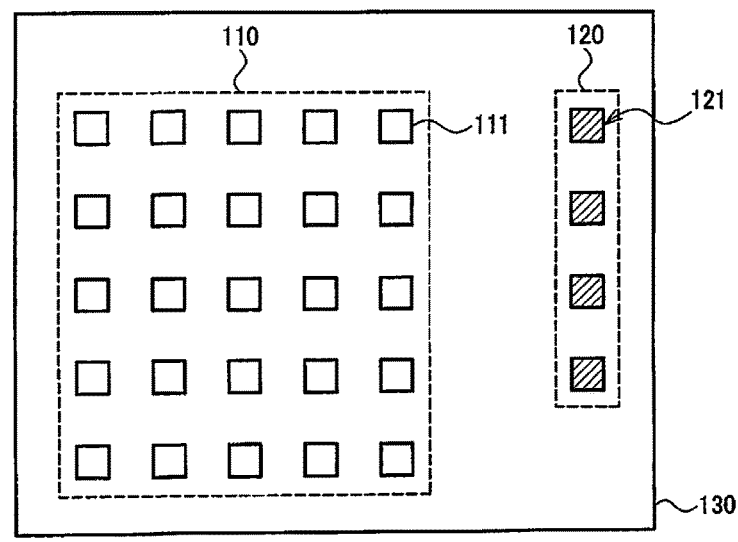
FIGS. 9A to 9C show examples of arrangement of an ultrasonic transducer element array and an identification ultrasonic transducer element array on a substrate.

Accordingly, the applicant of the invention proposes a method in which in addition to an ultrasonic transducer element array for measuring biological information, an ultrasonic transducer element array (identification ultrasonic transducer element array) for identification information (unique ID) is provided. Specifically, as shown in FIG. 3, the ultrasonic transducer device 100 according to the present embodiment includes an ultrasonic transducer element array 110 in which a plurality of ultrasonic transducer elements 111 are arranged, and an identification ultrasonic transducer element array 120 in which a plurality of identification ultrasonic transducer elements 121 are arranged. Note that although not shown in FIG. 3, the ultrasonic transducer device 100 according to the present embodiment includes a substrate 130 shown in FIG. 9A and the like, and the ultrasonic transducer element array 110 and the identification ultrasonic transducer element array 120 are provided on the substrate 130 as shown in FIG. 9A and the like. As shown in FIG. 4, the identification information of the ultrasonic transducer devices is set by some of the plurality of identification ultrasonic transducer elements 121 being set to a receivable state and the rest of the plurality of identification ultrasonic transducer elements 121 being set to a non-receivable state.

Here, the identification ultrasonic transducer elements 121 of the present embodiment include the element that is set to the non-receivable state, that is, the element that cannot actually output a sufficient electric signal even in response to an input of an ultrasonic wave. In other words, in the present embodiment, the identification ultrasonic transducer elements 121 do not refer to only elements that can receive an ultrasonic wave, but include an element in which a part of the structure constituting an ultrasonic wave receiving element is omitted or a part of the function of this structure constituting the element is limited. Note that a specific method for realizing the non-receivable state will be described later.

With this measure, the ultrasonic transducer device 100 can output its own identification information, and thus appropriate processing and management of biological information is possible. At that time, by the same manufacturing process as that of the ultrasonic transducer elements for measuring biological information, it is possible for the ultrasonic transducer device 100 to have identification information. Therefore, an increase in cost is suppressed and the manufacturing process is simplified, as compared to the case where a new memory for identification information or the like is added. Furthermore, in contrast to a memory or the like, the identification information according to the present embodiment is realized in a hardware manner, making it possible to suppress possible manipulation by a third party.

The following describes an example of a configuration of a system of the ultrasonic transducer device 100, the ultrasonic measurement device 300, and the like, according to the present embodiment. Then, specific configurations of the ultrasonic transducer elements 111 for measuring biological information and the identification ultrasonic transducer elements 121, examples of arrangement on the substrate, an example of connection of interconnects are described, and an example of a method for setting the identification ultrasonic transducer element 121 to the non-receivable state are described. Ultimately, processing in a processing unit 310 and the like that are included in the ultrasonic measurement device 300 is described in detail with reference to a flowchart and the like.

2. Example of System Configuration

As shown in FIG. 3, an example of a configuration of the ultrasonic transducer device 100 according to the present embodiment includes the ultrasonic transducer element array 110 and the identification ultrasonic transducer element array 120.

Furthermore, the method of the present embodiment is applicable to the ultrasonic measurement device 300 including the ultrasonic transducer device 100. As shown in FIG. 3, the ultrasonic measurement device 300 may include the processing unit 310 that acquires identification information of the ultrasonic transducer device 100 based on a signal received from the identification ultrasonic transducer element array 120.

Here, the processing unit 310 controls transmission of information (biological information) output from the ultrasonic transducer element array 110 and information (identification information) output from the identification ultrasonic transducer element array 120 in appropriate association with each other, to the outside. However, the processing unit 310 is not prohibited from performing detailed processing performed on the biological information, for example, processing for obtaining a blood pressure or processing for generating an ultrasonic image.

Figure 5:
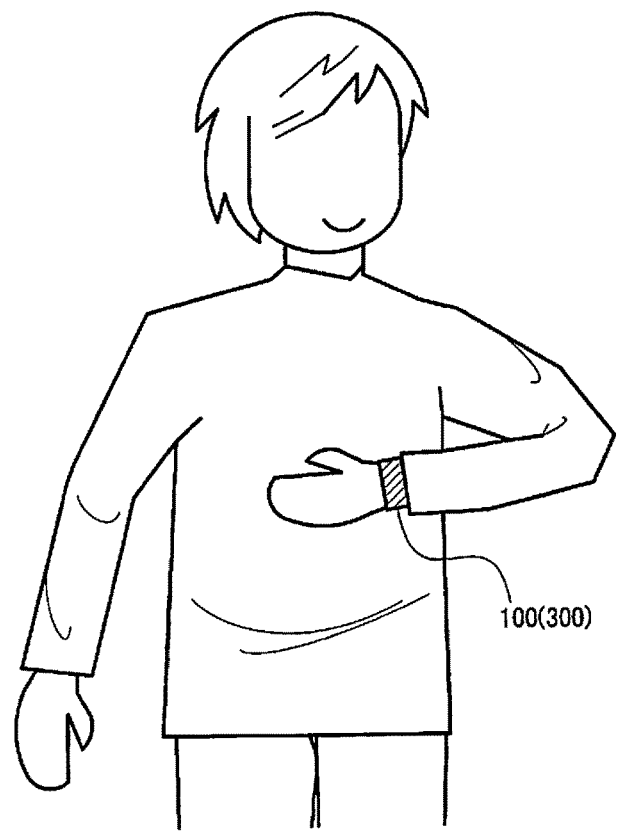
FIG. 5 shows a specific example of the ultrasonic measurement device according to the present embodiment.

Various specific shapes and usages of the ultrasonic measurement device 300 are conceivable, and the ultrasonic measurement device 300 may be, for example, a wristwatch-shaped device as shown in FIG. 5. The ultrasonic measurement device 300 is a device that measures a reflected ultrasonic wave so as to obtain biological information on a subject. FIG. 5 shows an example for measuring, as biological information, information on a blood vessel system function, such as the blood pressure of a blood vessel that is an artery or the thickness of the intima/media complex of a blood vessel (Intima Media Thickness: IMT), based on a result received in the ultrasonic transducer element array 110. In the example of the wristwatch-shaped device as shown in FIG. 5, particularly an artery in the wrist area is a target blood vessel that is to be measured.

Figure 6:
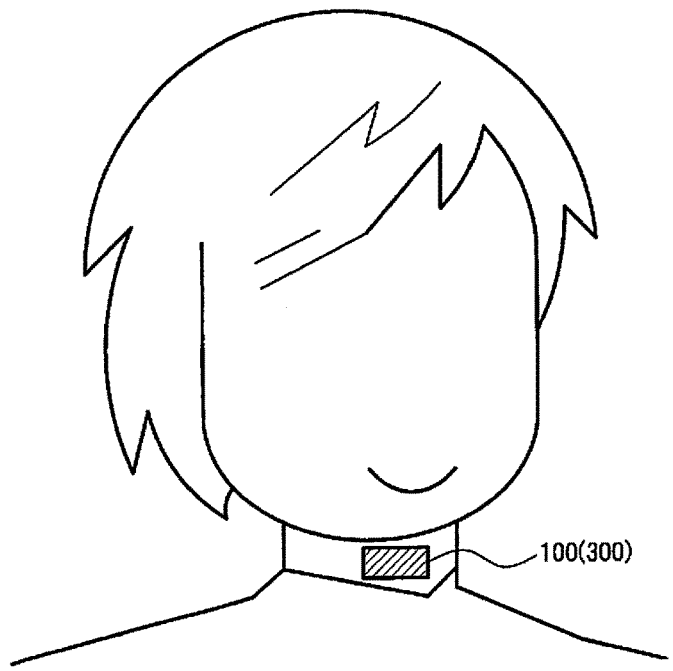
FIG. 6 shows a specific example of the ultrasonic measurement device according to the present embodiment.

However, the ultrasonic measurement device 300 is not limited to FIG. 5, and may be, for example, a device attached to the neck area of a user as shown in FIG. 6. As an example, it is conceivable that the ultrasonic measurement device 300 has a band-shaped support member such as a choker, and is fixed to the neck area of the user with the support member. Furthermore, instead of the use of the band-shaped support member, the ultrasonic transducer device 100 or the ultrasonic measurement device 300 itself may be configured to be adhesive to a biological body. Various modifications are possible for the attaching method by a user. In the case of a device that is attached to the neck area as shown in FIG. 6, the ultrasonic measurement device 300 measures the carotid artery as a target blood vessel that is to be measured.

Figure 7:
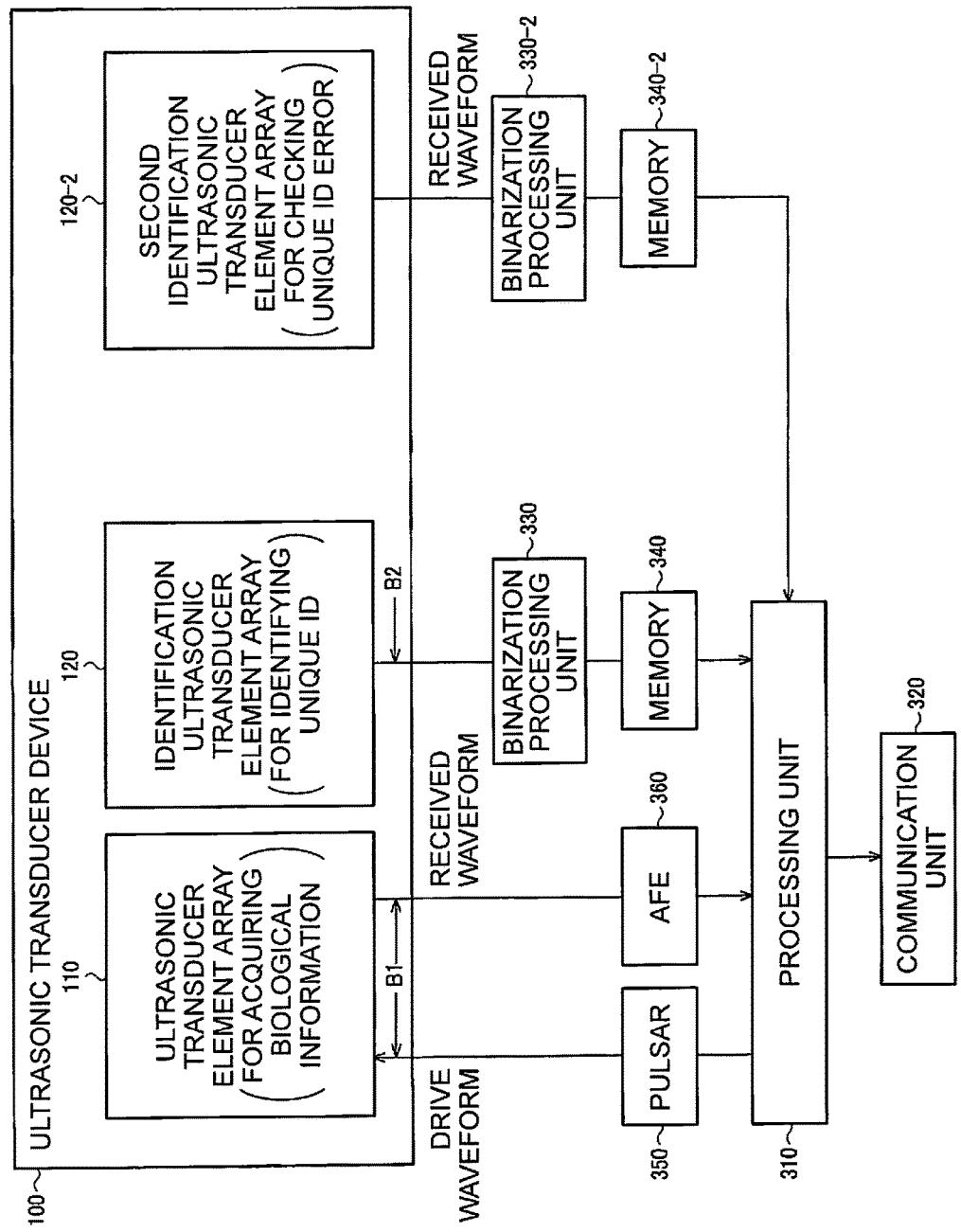
FIG. 7 shows an example of a detailed configuration of the ultrasonic measurement device according to the present embodiment.

Furthermore, FIG. 7 shows an example of a specific configuration of the ultrasonic measurement device 300. The ultrasonic measurement device 300 may further include a communication unit 320 that transmits a signal received by the ultrasonic transducer element array 110, with the identification information acquired by the processing unit 310 as a header.

Accordingly, it is possible, for example, to appropriately transmit the signal (biological information) received by the ultrasonic transducer element array 110 in association with the identification information to an external device.

Furthermore, as shown in FIG. 7, the ultrasonic measurement device 300 may include a binarization processing unit 330 that binarizes signals from the identification ultrasonic transducer elements 121 of the identification ultrasonic transducer element array 120, and a storage unit 340 (memory) in which the binarized signals are stored. Note that in this context, the memory is merely one for use in temporarily storing identification information, and values in the memory are appropriately updated based on outputs of the identification ultrasonic transducer element array 120 configured as hardware, and thus this memory does not reduce the security against manipulation of the identification information.

Furthermore, the ultrasonic measurement device 300 may include a pulsar 350 that outputs a drive waveform to the ultrasonic transducer element array 110, and an analog front end (AFE) 360 that connects the ultrasonic transducer element array 110 and the processing unit 310. The pulsar 350 and the AFE 360 are widely used structures, and thus detailed descriptions thereof are omitted.

Furthermore, the ultrasonic transducer device 100 according to the present embodiment may also include a second identification ultrasonic transducer element array 120-2, and in this case, the ultrasonic measurement device 300 may also include a binarization processing unit 330-2 and a storage unit 340-2 for the second identification ultrasonic transducer element array 120-2.

The second identification ultrasonic transducer element array 120-2 and the like are configured to check an error in identification information. Processing using information from the second identification ultrasonic transducer element array 120-2 will be described in detail later.

Furthermore, the method of the present embodiment is applicable to a ultrasonic measurement system that includes a plurality of ultrasonic transducer devices 100 each having set identification information, and an information processing device 200 for collecting, from each of the plurality of ultrasonic transducer devices 100, biological information with which the identification information on this ultrasonic transducer device is associated.

Here, each of the plurality of ultrasonic transducer devices 100 is a wearable ultrasonic transducer device that is attached to one of a plurality of subjects or to one of a plurality of areas of a subject, and the information processing device 200 identifies pieces of biological information that were received in the same period from the plurality of ultrasonic transducer devices.

In other words, the method of the present embodiment is applicable to the ultrasonic measurement system shown in FIGS. 1, 2A, 2B, and the like. In this case, the identification information is set by the identification ultrasonic transducer elements 121 of each of the plurality of ultrasonic transducer devices 100.

Accordingly, even in the case where the information processing device 200 acquires signals from a plurality of ultrasonic transducer devices in the same period, as shown in FIG. 1 and the like, it is possible to achieve realization of a system that appropriately performs processing and management of biological information by using identification information, and the like.

3. Ultrasonic Transducer Element and Identification Ultrasonic Transducer Element The following describes an example of a configuration of each of the elements included in the ultrasonic transducer device 100, an example of an arrangement of each element array, an example of a realization of the identification ultrasonic transducer element array 120, and a specific example of the method for setting the identification ultrasonic transducer element 121 to the non-receivable state.

3.1 Example of Configuration of Element

Figure 8A:
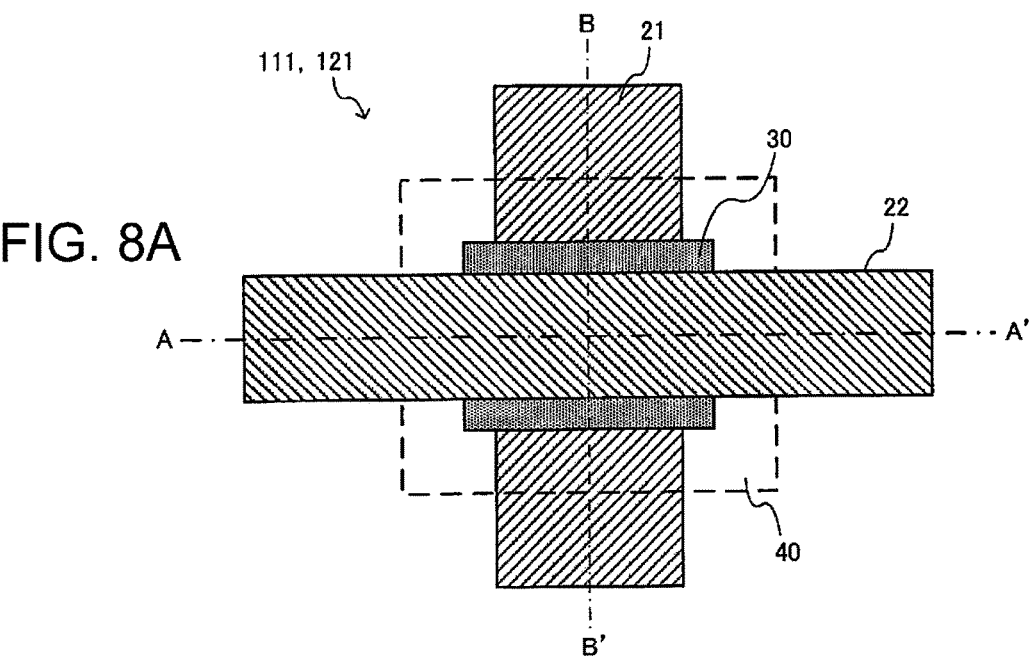
FIGS. 8A to 8C show examples of configurations of an ultrasonic transducer element and the identification ultrasonic transducer element.
Figure 8B:
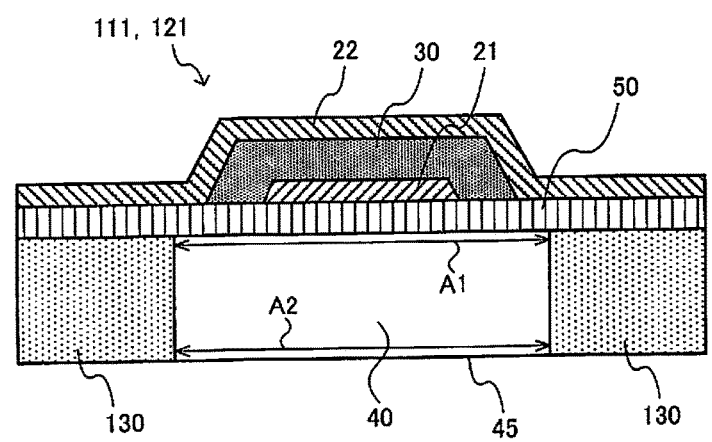
Figure 8C:
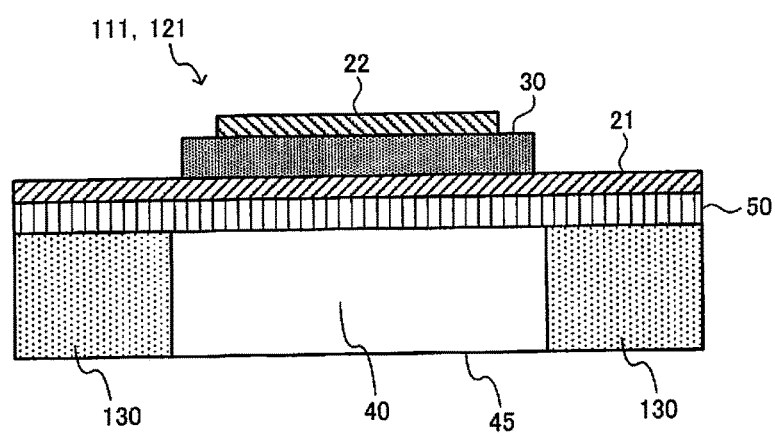

FIGS. 8A to 8C show examples of configurations of each of the plurality of ultrasonic transducer elements 111 constituting the ultrasonic transducer element array 110, and each of the plurality of identification ultrasonic transducer elements 121 constituting the identification ultrasonic transducer element array 120. Note that although the following illustrates an example of a configuration of the ultrasonic transducer element 111, the identification ultrasonic transducer element 121 can also be realized by the same configuration.

The ultrasonic transducer element 111 includes a vibrating membrane (membrane or support member) 50 and a piezoelectric element unit. The piezoelectric element unit includes a first electrode layer (lower electrode) 21, a piezoelectric body layer (piezoelectric body film) 30, and a second electrode layer (upper electrode) 22.

FIG. 8A is a plan view illustrating the ultrasonic transducer element 111 formed on the substrate (silicon substrate) 130 when viewed in a direction perpendicular to the substrate 130 on which the element is formed. FIG. 8B is a cross-sectional view taken along the line A-A' of FIG. 8A. FIG. 8C is a cross-sectional view taken along the line B-B' of FIG. 8A.

The first electrode layer 21 is formed from a thin metal film on the vibrating membrane 50. This first electrode layer 21 may be an interconnect that extends outward from the element formation region as shown in FIG. 8A and is connected to an adjacent ultrasonic transducer element 111.

The piezoelectric body layer 30 is made from, for example, a zirconate titanate (PZT) thin film, and is provided so as to cover at least a part of the first electrode layer 21. Note that the material of the piezoelectric body layer 30 is not limited to PZT, and may be, for example, lead titanate ($PbTiO_3$), lead zirconate ($PbZrO_3$), lead lanthanum titanate ((Pb, La) $TiO_3$), or the like.

The second electrode layer 22 is made from, for example, a thin metal film, and is provided so as to cover at least a part of the piezoelectric body layer 30. This second electrode layer 22 may be an interconnect that extends outward from the element formation region as shown in FIG. 8A and is connected to an adjacent ultrasonic transducer element 111.

The vibrating membrane (membrane) 50 has a two-layer configuration of, for example, a $SiO_2$ thin film and a $ZrO_2$ thin film, and is provided so as to close an opening 40. This vibrating membrane 50 supports the piezoelectric body layer 30 and the first and second electrode layers 21 and 22, and can vibrate in accordance with expansion and contraction of the piezoelectric body layer 30 so as to generate an ultrasonic wave.

The opening 40 is formed by the rear surface (on which no element is formed) of the substrate (silicon substrate) 130 being etched by reactive ion etching (RIE) or the like. The resonance frequency of the ultrasonic wave depends on the size denoted by "A1" of a diaphragm of FIG. 8B. Here, the diaphragm refers to a structure that detects a pressure and is realized by a part of the vibrating membrane 50 that closes the opening 40.

At that time, in the case where the substrate is processed to have vertical side surfaces as shown in FIG. 8B, the size denoted by "A2" of an open part 45 of the opening 40 and the size denoted by "A1" of the diaphragm match each other (or have almost the same size). That is, in this example of FIG. 8B, the resonance frequency of the ultrasonic wave depends on the size of the open part 45 of the opening 40, and the ultrasonic wave is emitted to the piezoelectric body layer 30 side (in the direction toward the viewer of the drawing of FIG. 8A).

The lower electrode (first electrode) of the ultrasonic transducer element 111 is formed by the first electrode layer 21, and the upper electrode (second electrode) is formed by the second electrode layer 22. Specifically, the part of the first electrode layer 21 that is covered with the piezoelectric body layer 30 forms the lower electrode, and the part of the second electrode layer 22 that covers the piezoelectric body layer 30 forms the upper electrode. That is, the piezoelectric body layer 30 is provided between the lower electrode and the upper electrode.

As described above, the identification ultrasonic transducer element array 120 can also be formed by the same processes as those of the ultrasonic transducer element array 110. That is, the identification ultrasonic transducer element 121 has also the configuration of FIGS. 8A to 8C.

3.2 Example of Arrangement of Each Element Array on Substrate or the Like

Various examples of an arrangement of the ultrasonic transducer element array 110 and the identification ultrasonic transducer element array 120 on the substrate according to the present embodiment are conceivable. For example, the ultrasonic transducer element array 110 is arranged in a first region of the substrate 130 in a plan view in the thickness direction of the substrate, and the identification ultrasonic transducer element array 120 may be arranged in a second region of the substrate 130 in the plan view.

Here, the second region refers to a region different from the first region of the substrate 130. Furthermore, the thickness direction of the substrate 130 refers to a direction of crossing (in a more limited sense, perpendicular to) the surface of the substrate 130 on which the elements and the like are arranged. For example, assume that the substrate 130 is a rectangular parallelepiped whose sides have the lengths X, Y, and Z, and X>Z and Y>Z are satisfied, the thickness direction of the substrate 130 is a direction along the side having the length Z. FIG. 9A is a diagram illustrating an example of arrangement of the ultrasonic transducer element array 110 and the identification ultrasonic transducer element array 120 when the substrate 130 is viewed in plan view in the thickness direction, and FIG. 9B is a cross-sectional view of the substrate 130 viewed from the side.

As an example, when, as shown in FIG. 9A, the substrate 130 is divided into a region on a first direction (leftward direction of FIG. 9A) side and a region on a second direction (rightward direction of FIG. 9A) side opposite to the first direction, the first region may be a part or all of the region on the first direction side, and the second region may be a part or all of the region on the second direction side.

Figure 9B:
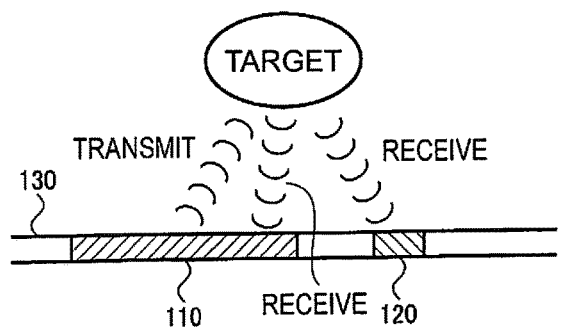
Figure 9C:
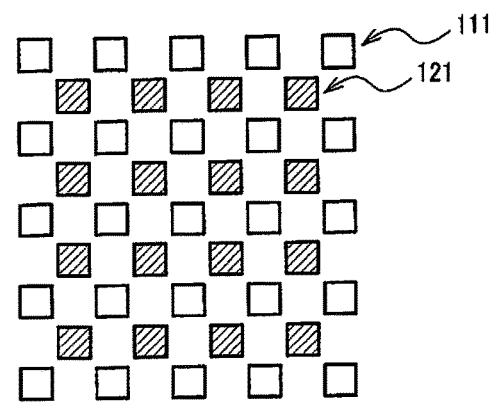

Alternatively, as shown in FIG. 9C, the plurality of identification ultrasonic transducer elements 121 may also be arranged among the plurality of ultrasonic transducer elements 111. Similarly to FIG. 9A, FIG. 9C is a diagram of the substrate 130 viewed in plan view in the thickness direction.

As shown in FIG. 9B, in the present embodiment, the identification ultrasonic transducer element array 120 is assumed to receive an echo signal of an ultrasonic wave from the ultrasonic transducer element array 110, the echo signal of an ultrasonic wave serving as a received signal. In this case, the processing unit 310 of the ultrasonic measurement device 300 acquires identification information based on the received signal received by the identification ultrasonic transducer element array 120.

Since, as shown in FIGS. 8A to 8C, the identification ultrasonic transducer elements 121 have the same configuration as that of the ultrasonic transducer elements 111, the identification ultrasonic transducer element array 120 can also output an ultrasonic wave. However, the ultrasonic transducer element array 110 receives a signal resulting from this ultrasonic wave being reflected on the biological body, leading to a risk that inappropriate biological information is acquired. That is, it is considered to be advantageous that outputting an ultrasonic wave is limited to the ultrasonic transducer element array 110.

In this case, taking into consideration the strength of an echo signal received by each element of the identification ultrasonic transducer element array 120, the arrangement of the arrays in a mixed manner as shown in FIG. 9C is advantageous in terms of the signal strength as compared with the arrangement of the arrays in different regions as shown in FIG. 9B, because the transmission route of the ultrasonic wave is shorter.

On the other hand, in the method of the present embodiment as described later, interconnects are provided for the respective identification ultrasonic transducer elements 121. Therefore, it is necessary to provide a region for the interconnect in the periphery of each identification ultrasonic transducer element 121, and in the arrangement as shown in FIG. 9B, the space is ensured with difficulty or the array gap of the ultrasonic transducer element array 110 may be shifted in order to ensure the space. In this respect, the arrangement shown in FIG. 9A is more advantageous.

Furthermore, a modification of the present embodiment in which the identification ultrasonic transducer element array 120 outputs an ultrasonic wave can be performed. That is, each element array cannot have the most appropriate arrangement that can cover every situation, and it is preferable to determine the arrangement taking into consideration various situations.

3.3 Example of Realization of Identification Ultrasonic Transducer Element Array As is clear from FIG. 7 and the like, the ultrasonic transducer device 100 according to the present embodiment includes first signal lines (for example, interconnects that realize electrical connections "B1" of FIG. 7) for the ultrasonic transducer element array 110 and a second signal line (for example, an interconnect that realizes an electrical connection "B2" of FIG. 7) for the identification ultrasonic transducer element array 120, the second signal line being different from the first signal lines.

By this configuration, it is possible to prevent biological information and identification information from being mixed. Therefore, the processing unit 310 of the ultrasonic measurement device 300 can process and use the respective types of information separately such that the identification information is used as a header of the biological information.

Also, second signal lines may be connected to the respective identification ultrasonic transducer elements 121 independently therefrom. FIG. 4 is a diagram illustrating the concept of the identification information in the ultrasonic measurement device 300 including the ultrasonic transducer device 100 according to the present embodiment. In the example of FIG. 4, the identification ultrasonic transducer element array 120 includes eight identification ultrasonic transducer elements 121-1 to 121-8, which are respectively connected to the binarization processing unit 330 by independent interconnects.

It is assumed that such interconnection is made and each element is set to the receivable state or the non-receivable state. If an ultrasonic wave is input, the element (for example, element 121-1) set in the receivable state outputs a signal of some sort, whereas the element (for example, element 121-2) set in the non-receivable state does not output any significant signal. Therefore, when binarization is performed such that, for example, the state in which a signal is output is defined as "1" and the state in which no signal is output is defined as "0", a signal having the number of bits that equals to the number of the identification ultrasonic transducer elements can be obtained. In the present embodiment, this signal may be used as identification information.

In FIG. 4, since the elements 121-1, 121-4, 121-6, and 121-8 are in the receivable state and the other elements are in the non-receivable state, an 8-bit signal "10010101" in the case where the bit sequence is arranged in the order shown in FIG. 4 serves as an identification signal. That is, by using N identification ultrasonic transducer elements, N-bit identification information can be generated, making it possible to identify up to $2^N$ ultrasonic transducer devices 100 from each other.

Here, each of the plurality of identification ultrasonic transducer elements 121 needs only to generate, when being set in the receivable state, a reception voltage in response to a given ultrasonic wave. Therefore, it is sufficient that a resonance frequency is set such that an ultrasonic wave (for example, a reflected ultrasonic wave transmitted from the ultrasonic transducer element array 110) that serves as an input can be received, and the resonance frequencies of the identification ultrasonic transducer elements 121 may be the same or different from each other. However, since the resonance frequency depends on the size of the diaphragm as described above with reference to FIGS. 8A to 8C, it is preferable that the resonance frequencies of the elements correspond to each other (in a more limited sense, match each other), taking into consideration an efficient arrangement of the identification ultrasonic transducer elements 121 on the substrate.

Note that the ultrasonic transducer device according to the present embodiment can be seen in another viewpoint. Specifically, as shown in FIG. 4, the ultrasonic transducer device according to the present embodiment includes an ultrasonic transducer element array (array 120 in the example of FIG. 4) in which a plurality of ultrasonic transducer elements (elements 121-1 to 121-8 in the example of FIG. 4) are arranged, and some of the plurality of ultrasonic transducer elements are set to the receivable state and connected to a first signal line, and the rest of the plurality of ultrasonic transducer elements are set to the non-receivable state and connected to a second signal line, and signal terminals that are connected to the second signal line are electrically independent from the first signal line.

Accordingly, it is possible to handle the receivable elements and the non-receivable elements as being electrically independent. As described above, in the present embodiment, useful information (in a more limited sense, identification information) is generated by both a condition in which an electric signal is appropriately output from the receivable elements and a condition in which no significant electric signal is output from the non-receivable elements being satisfied. Therefore, no appropriate output of identification information is possible in the situation in which an output of the receivable element and an output of the non-receivable element are mixed in a single output terminal. In other words, in order to appropriately generate identification information, it is necessary to handle the receivable elements and the non-receivable elements as being electrically independent, and in order to achieve this, a configuration is possible in which different signal lines are used for a receivable element and a non-receivable element, and the terminals of the respective signal lines are electrically independent from each other.

In the example of FIG. 4, the plurality of ultrasonic transducer elements 121-1 to 121-8 constituting the ultrasonic transducer element array are not only classified into receivable elements and non-receivable elements but also handled as independent elements in a finer manner. Specifically, eight signal lines L1 to L8 corresponding to the eight elements are provided. Furthermore, terminals Ti1 and Ti2 (i=1 to 8) of the i-th signal line are electrically independent from terminals Tk1 and Tk2 (k=1 to 8, and k≠i) of the k-th signal line. In this case, the above-described first signal line corresponds to the signal lines L1, L4, L6, and L8, the second signal line corresponds to the signal lines L2, L3, L5, and L7, and the signal terminals of the first signal line and the signal terminals of the second signal line are electrically independent from each other.

3.4 Specific Example of Method for Setting Identification Ultrasonic Transducer Element to Non-Receivable State As described above with reference to FIGS. 8A to 8C, each identification ultrasonic transducer element 121 according to the present embodiment receives an ultrasonic wave by the diaphragm realized by the corresponding opening 40 and vibrating membrane 50 transmitting a pressure to the piezoelectric body layer 30. That is, in the state in which this diaphragm is not configured or does not sufficiently function, an electric signal is not output even when an ultrasonic wave is incident, making it possible to realize the non-receivable state.

Figure 10A:
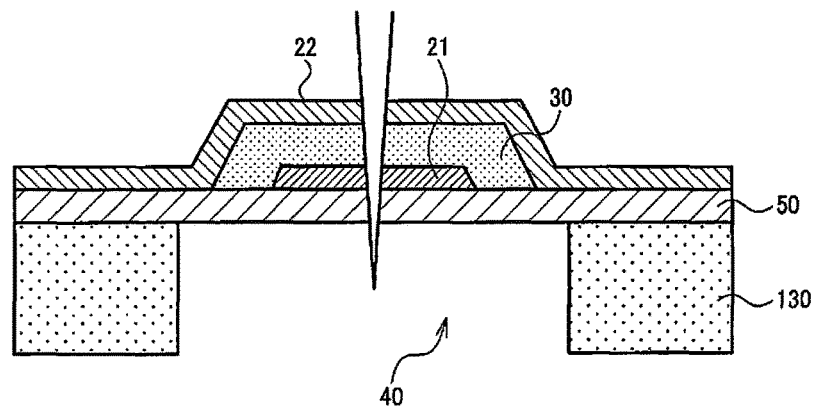
FIGS. 10A to 10C are diagrams illustrating a method for setting the identification ultrasonic transducer element to a non-receivable state.

Therefore, as shown in FIG. 10A, it is sufficient to, for example, physically damage the piezoelectric body layer 30 and the vibrating membrane 50 that closes the opening 40. In FIG. 10A, the element is damaged by sticking a projection like a needle into the substrate 130 from the side on which the piezoelectric body layer 30 is provided. Note that the non-receivable state can be realized when the element is damaged to the extent of not functioning, and thus any device and direction may be used in damaging the element. Furthermore, FIG. 10A shows an example in which the element having a completed structure is damaged, but a modification in which an element is damaged at an earlier timing (for example, before formation of electrodes) can be performed.

Alternatively, the vibrating membrane 50 and the like may not be damaged since it is sufficient that the diaphragm does not transmit a sufficient pressure. For example, each of the rest of the identification ultrasonic transducer elements 121 (that are set to the non-receivable state) may also be set to the non-receivable state by a vibration suppression material.

Here, the vibration suppression material refers to a material having a higher hardness and toughness, and examples thereof include a thermosetting resin such as an epoxy resin.

Figure 10B:
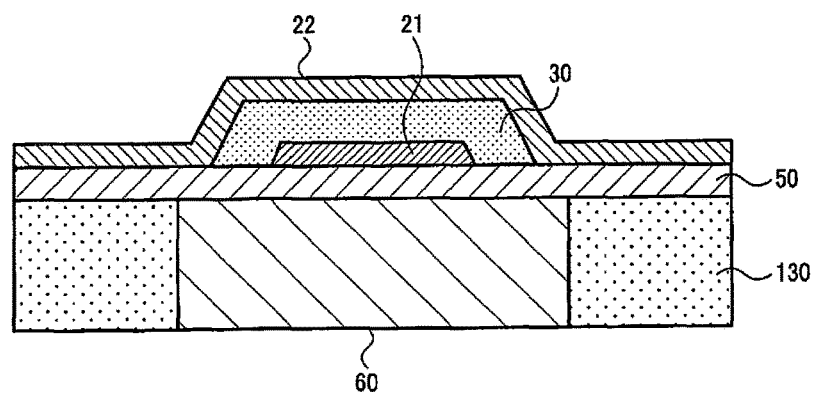
Figure 10C:
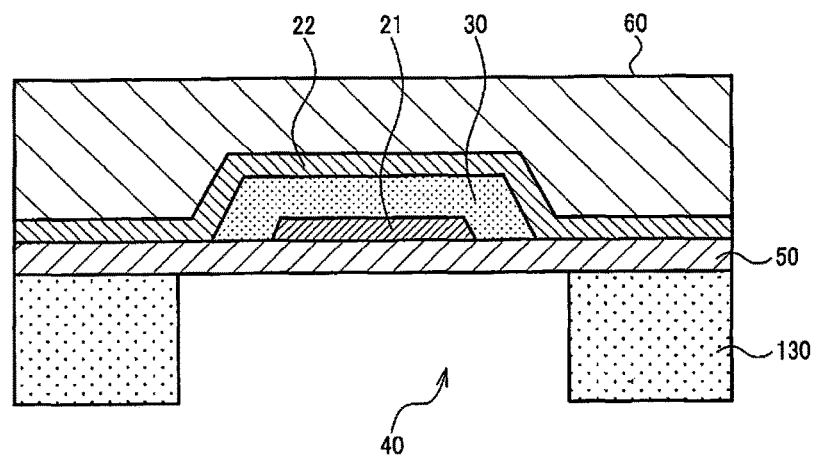

Specifically, the vibration suppression material needs only to be provided so as to prevent a particular part of the vibrating membrane 50 that closes the opening 40 from vibrating, and as shown in, for example, FIG. 10B, a vibration suppression material 60 may be provided so as to fill up the opening 40. Alternatively, as shown in FIG. 10C, the vibration suppression material 60 may be applied from the electrode side or the piezoelectric body layer 30 side so as to cover these structures. In both cases, vibration will be suppressed, and thus the identification ultrasonic transducer element 121 will not output an electric signal even if an ultrasonic wave is input.

Alternatively, the opening 40 may not originally be formed. As described above, the identification ultrasonic transducer element array 120 includes the vibrating membranes 50 formed on the substrate 130, and the piezoelectric elements (piezoelectric element units including the first electrode layer 21, the piezoelectric body layer 30, and the second electrode layer 22) formed on the vibrating membrane 50. In this case, each of some identification ultrasonic transducer elements 121 is set to the receivable state by the corresponding opening being formed in the substrate 130, and each of the rest of the identification ultrasonic transducer elements 121 is set to the non-receivable state by the corresponding opening being not formed in the substrate 130.

As described above, the diaphragm is realized by the opening 40 and the vibrating membrane 50 that closes the opening 40. That is, if no opening 40 is formed, it will be possible to set the corresponding identification ultrasonic transducer element 121 to the non-receivable state.

As described above with reference to FIGS. 8A to 8C, the opening 40 is formed by, for example, etching the substrate 130. In the etching process, processing is performed such that a resist is not applied to a position at which the opening 40 is to be formed but applied to the remaining place. That is, it is sufficient that a resist is applied not to the position corresponding to the identification ultrasonic transducer element 121 that is desired to be set to the receivable state but to the position corresponding to the identification ultrasonic transducer element 121 that is desired to be set to the non-receivable state.

In the present embodiment, it is conceivable that a unique ID is given to each ultrasonic transducer device 100. Therefore, if there are N devices, there will be N patterns of the resist. Although the N patterns may be formed directly, each pattern has a low applicability leading to a reduction in productivity:

Therefore, a configuration is possible in which a resist is first applied using a pattern for forming the openings 40 at the positions that correspond to all the identification ultrasonic transducer elements 121, and then a resist is applied to individual positions that corresponds to the elements that are desired to be set to the non-receivable state. That is, opening formation, which is realized by resist application and etching processes, is realized by a first resist application process, a second resist application process, and an etching process. Here, in the first resist application process, since it is sufficient to use the pattern for forming all the openings as described above, this process is performed on all the ultrasonic transducer devices 100. Furthermore, the second resist application process is performed differently for each device, but this can be easily realized by applying a resist to the positions corresponding to the elements that are desired to be set to the non-receivable state using a dispenser or the like, and thus the burden to realize the process is not large.

Figure 11A:
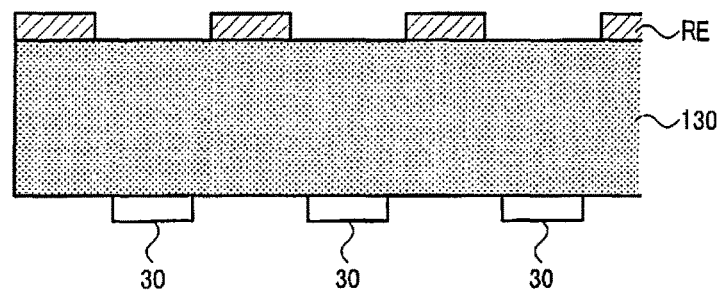
FIGS. 11A to 11D are diagrams illustrating a method for setting the identification ultrasonic transducer element to the non-receivable state depending on whether or not an opening is formed.
Figure 11B:
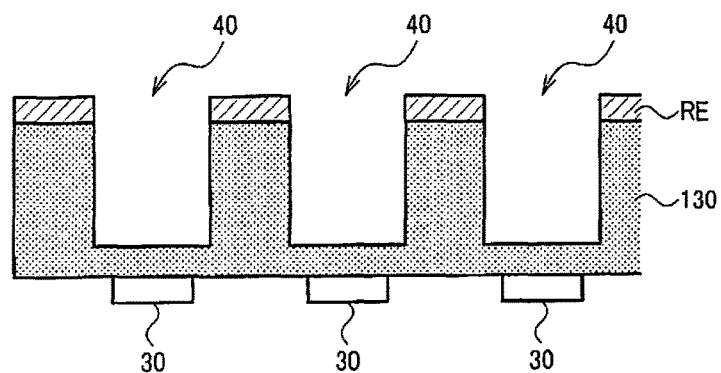

This is illustrated in FIGS. 11A to 11D. FIG. 11A shows the first resist application process, in which a resist RE is not applied to the positions that corresponds to all the identification ultrasonic transducer elements 121 (three identification ultrasonic transducer elements in FIG. 11A). Therefore, by performing etching process directly thereafter, the openings 40 are formed at all of the three positions as shown in FIG. 11B.

Figure 11C:
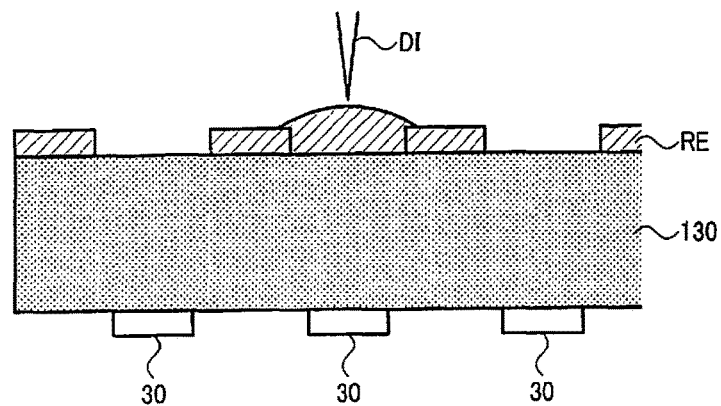
Figure 11D:
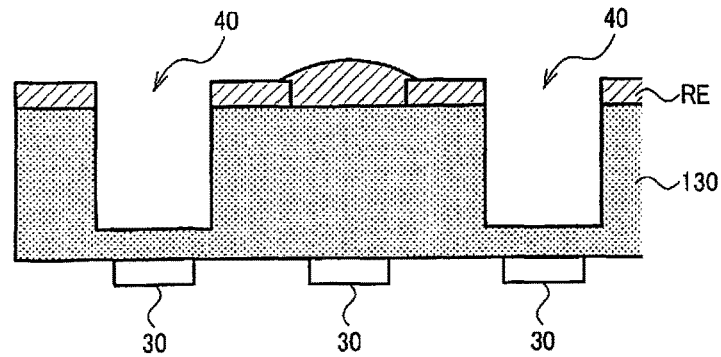

In contrast, when the central element is desired to be set to the non-receivable state, after the process shown in FIG. 11A, the resist RE needs only to be applied again to a desired position using a dispenser DI or the like, as shown in FIG. 11C. With this measure, the situation as shown in FIG. 11D is achieved by the etching process, in which the openings 40 are formed in the elements (left and right elements in the example of FIG. 11D) that are desired to be set to the receivable state, whereas no opening 40 is formed in the central element that is desired to be set to the non-receivable state.

4. Detail of Processing

Figure 12:
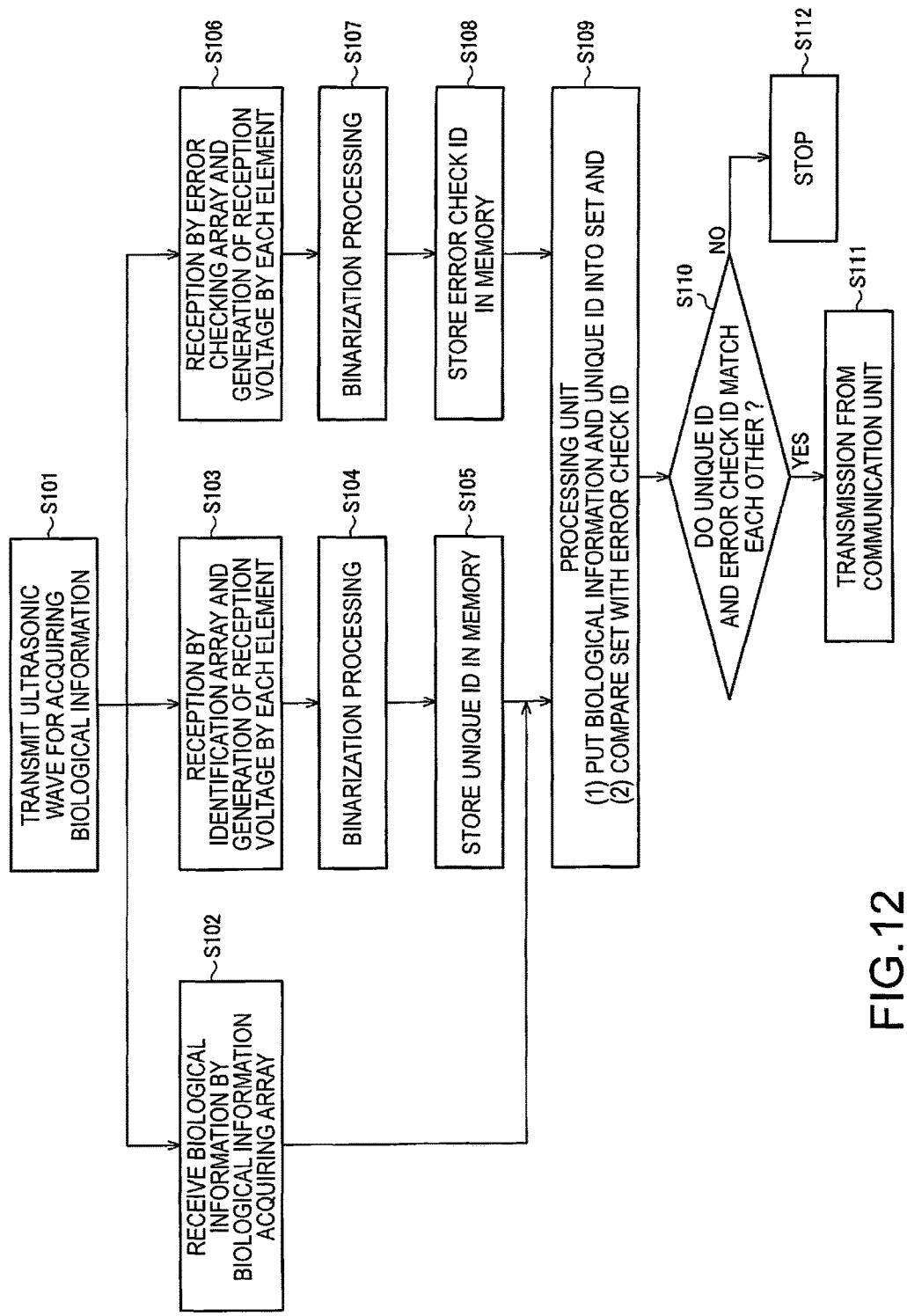
FIG. 12 is a flowchart illustrating the processing of the present embodiment.

Hereinafter, processing in the processing unit 310 of the ultrasonic measurement device 300 in the present embodiment will be described in detail with reference to the flowchart of FIG. 12. Note that the flowchart of FIG. 12 is assumed to show the processing of a configuration as shown in FIG. 7 that includes the second identification ultrasonic transducer element array 120-2, which is an array for checking an error, but the array may be omitted as described above. When the second identification ultrasonic transducer element array 120-2 is omitted, the processing regarding error checking in the processing unit 310 will also be omitted. Furthermore, the flowchart of FIG. 12 includes operation steps of the element arrays such as step S102 and the like, and thus not all the steps are performed in the processing unit 310.

At the start of this processing, an ultrasonic wave for acquiring biological information is first transmitted (S101). This can be realized, as described above, by the ultrasonic transducer element array 110 transmitting an ultrasonic wave. Then, the ultrasonic wave transmitted in step S101 is reflected on a biological body, and is received by each element array.

Specifically, the array for acquiring biological information, that is, the above-described ultrasonic transducer element array 110 receives biological information based on the reflected ultrasonic wave (step S102).

Furthermore, the identification array, that is, the above-described identification ultrasonic transducer element array 120 performs reception, and each identification ultrasonic transducer element 121 generates a reception voltage (step S103). Note that, in step S103, the elements set to the receivable state generate a significant reception voltage, whereas the elements set to the non-receivable state do not generate a reception voltage.

Then, the voltage of each element is subjected to binarization processing (step S104), and the binarized values are stored in the storage unit 340 (memory) as a unique ID (step S105). As described above, by setting different values for the binarized value (for example, 1) of the element that is set to the receivable state and generates a significant reception voltage, and the binarized value (for example, 0) of the element that is set to the non-receivable state and does not generate a reception voltage, the unique ID stored in the storage unit 340 is represented as a bit sequence that corresponds to receivable and non-receivable states of the identification ultrasonic transducer element array 120.

That is, in the present embodiment, identification information is acquired based on the presence or absent of a received signal from each of the plurality of identification ultrasonic transducer elements 121.

Furthermore, when an error check array, that is, the above-described second identification ultrasonic transducer element array 120-2 is provided, the array receives the reflected ultrasonic wave transmitted in step S101 (step S106), the reception voltage is subjected to binarization processing (S107), and a result of the binarization processing is stored in the memory (S108). Here, the information stored in step S108 is an ID for use in error checking.

Then, after steps S102, S105, and S108, the processing unit 310 performs processing for associating the biological information acquired in step S102 with the identification information (unique ID) stored in step S105. Furthermore, the unique ID stored in step S105 is compared with the error check ID stored in step S108 (S109)

Here, associating the biological information with the identification information may be, for example, processing for forming a data structure that corresponds to a communication protocol at the time of transmitting the biological information to another device. As an example, identification information may be given, as a header, to each minimum unit (for example, a packet) of data according to the communication protocol. In this case, each packet is configured to include identification information, which serves as a header part, and biological information, which is a data part (in a more limited sense, a part of biological information that is divided in a data amount that is included in the packet size).

Alternatively, a data structure may be used in which identification information is given to each of data units, the data unit in the situation in which biological information is measured or used serving as a reference. For example, when a fat and the like in the abdominal area is observed, it is possible to create and display an ultrasonic image of a given range of a biological body by transmitting an ultrasonic wave so as to be swept over a given range. In this case, the identification information may be given to each of units of biological information, biological information of one sweep of ultrasonic wave transmission or biological information of one ultrasonic image being the unit of the biological information.

Furthermore, each element of the second identification ultrasonic transducer element array 120-2 of the present embodiment is set to the receivable state or the non-receivable state by the same pattern as that of the identification ultrasonic transducer element array 120. Therefore, if reception voltages are correctly generated in the elements, the unique ID and the error check ID will match each other. That is, in a more limited sense, the comparison in step S109 between the unique ID and the error check ID is to determine whether or not the unique ID and the error check ID match each other.

As shown in FIG. 10A, when an element is damaged, the element is set to the non-receivable state. That is, it may be possible that an element that was originally set to the receivable state is shifted to the non-receivable state due to any reason. A case is conceivable, although the realization possibility is low, where an element that is considered to have been set to the non-receivable state is set in the receivable state due to damage or insufficient application of a vibration suppression material. In this case, the unique ID will change, and thus it is not possible to appropriately identify the ultrasonic transducer device 100. The error check ID enables, in such a situation, detection of at least an occurrence of an error.

Specifically, it is determined whether or not the unique ID and the error check ID match each other (step S110), and if they match each other, it is determined that there is no error regarding the unique ID, and the identification information and the biological information that were associated with each other in step S109 are transmitted from the communication unit 320. On the other hand, if No in step S110, it is determined that an error regarding the unique ID is possibly occurring, and the procedure is stopped (step S112).

Note that the error checking method is not limited to this, and may be executed in a modification in which the receivable and non-receivable states of the elements of the second identification ultrasonic transducer element array 120-2 are set so as to be parity bits of the unique ID, or to begin with, an element of a parity bit is added to the identification ultrasonic transducer element array 120.

Note that although the present embodiment has been described above, it can readily be appreciated by those skilled in the art that various modifications are possible without substantially departing from the novel features and effects of the invention. Therefore, all the modifications are included in the scope of the invention. For example, in the specification or drawings, a term that is described at least once together with a different term having wider scope and the same meaning can be replaced by the different term in any position in the specification or drawings. Furthermore, the configurations and operations of the ultrasonic transducer device, the ultrasonic measurement device, and the like are not limited to those described in the present embodiment, and various modifications are possible.

The entire disclosure of Japanese Patent Application No. 2014-173769 filed on Aug. 28, 2014 is expressly incorporated by reference herein.

What is claimed is:

1. An ultrasonic transducer device comprising:
    a substrate;
    an ultrasonic transducer element array that is provided on the substrate and in which a plurality of ultrasonic transducer elements are arranged; and
    an identification ultrasonic transducer element array that is provided on the substrate and in which a plurality of identification ultrasonic transducer elements are arranged,
    wherein identification information of the ultrasonic transducer device is encoded by arrangement of the plurality of identification ultrasonic transducer elements, some of the plurality of identification ultrasonic transducer elements being set to a receivable state, and the rest of the plurality of identification ultrasonic transducer elements being set to a non-receivable state.

2. The ultrasonic transducer device according to claim 1,
    wherein the identification ultrasonic transducer element array includes a vibrating membrane formed on the substrate and a piezoelectric element formed on the vibrating membrane,
    each of the identification ultrasonic transducer elements that are set to the receivable state has an opening formed in a corresponding position of the substrate where the identification ultrasonic transducer element is located, and
    each of the identification ultrasonic transducer elements that are set to the non-receivable state does not have an opening formed in a corresponding position of the substrate where the identification ultrasonic transducer element is located.

3. An ultrasonic measurement device comprising the ultrasonic transducer device according to claim 2.

4. The ultrasonic measurement device according to claim 3,
    wherein the processing unit acquires the identification information based on the presence or absence of the received signal from each of the plurality of identification ultrasonic transducer elements.

5. The ultrasonic measurement device according to claim 3,
    wherein the identification ultrasonic transducer element array receives, as the received signal, an echo signal of an ultrasonic wave from the ultrasonic transducer element array, and
    the processing unit acquires the identification information based on the received signal received by the identification ultrasonic transducer element array.

6. The ultrasonic measurement device according to claim 3, further comprising:
    a communication unit that transmits a received signal received by the ultrasonic transducer element array with the identification information acquired by the processing unit as a header.

7. The ultrasonic transducer device according to claim 1,
    wherein each of the identification ultrasonic transducer elements that are set to the non-receivable state is set to the non-receivable state by a vibration suppression material.

8. An ultrasonic measurement device comprising the ultrasonic transducer device according to claim 7.

9. The ultrasonic transducer device according to claim 1,
    wherein the plurality of ultrasonic transducer elements are arranged in a first region of the substrate in a plan view in a thickness direction of the substrate, and the plurality of identification ultrasonic transducer elements are arranged in a second region of the substrate in the plan view.

10. An ultrasonic measurement device comprising the ultrasonic transducer device according to claim 9.

11. The ultrasonic transducer device according to claim 1, wherein the plurality of identification ultrasonic transducer elements are arranged among the plurality of ultrasonic transducer elements.

12. An ultrasonic measurement device comprising the ultrasonic transducer device according to claim 11.

13. The ultrasonic transducer device according to claim 1, further comprising:
   a first signal line for the ultrasonic transducer element array; and
   a second signal line for the identification ultrasonic transducer element array, the second signal line being different from the first signal line.

14. An ultrasonic measurement device comprising the ultrasonic transducer device according to claim 13.

15. An ultrasonic measurement device comprising the ultrasonic transducer device according to claim 1.

16. The ultrasonic measurement device according to claim 15, further comprising:
   a processing unit that acquires identification information of the ultrasonic transducer device based on a received signal from the identification ultrasonic transducer element array.

* * * * *